United States Patent [19]

Bisch

[11] Patent Number: 5,217,011
[45] Date of Patent: Jun. 8, 1993

[54] METHOD AND APPARATUS FOR TRANSDERMAL COMMUNICATION

[75] Inventor: Michael E. Bisch, Kirkwood, Mo.

[73] Assignee: Storz Instrument Company, St. Louis, Mo.

[21] Appl. No.: 368,602

[22] Filed: Jun. 20, 1989

[51] Int. Cl.⁵ .................. A61N 1/00; H04R 25/00
[52] U.S. Cl. .................. 128/420.6; 128/419 R; 128/419 P; 128/631; 600/25; 623/11; 381/68; 340/870.31
[58] Field of Search .... 128/420.6, 419 R, 419 PG:419 PT, 128/420.5, 904, 631, 419 P; 600/25, 27; 623/10, 11, 16, 24; 381/68; 340/870.31

[56] References Cited

U.S. PATENT DOCUMENTS

| | | | |
|---|---|---|---|
| 3,752,939 | 8/1973 | Bartz | 600/25 |
| 3,764,748 | 10/1973 | Branch | 600/25 |
| 4,062,354 | 12/1977 | Taylor et al. | 128/631 |
| 4,142,533 | 3/1979 | Brownlee et al. | 128/419 PT |
| 4,294,262 | 10/1981 | Williams | 73/861.79 |
| 4,301,804 | 11/1981 | Thompson et al. | 128/419 PG |
| 4,495,953 | 1/1985 | Bennewitz | 128/789 |
| 4,571,589 | 2/1986 | Slocum et al. | 128/631 X |
| 4,606,329 | 8/1986 | Hough | 600/25 |
| 4,611,127 | 9/1986 | Ibrahim et al. | 340/551 X |
| 4,641,633 | 2/1987 | Delgado | 600/13 |
| 4,850,962 | 7/1989 | Shaefer | 600/25 |
| 4,957,478 | 9/1990 | Maniglia | 623/10 X |

Primary Examiner—Richard J. Apley
Assistant Examiner—Joe H. Cheng
Attorney, Agent, or Firm—Brooks & Kushman

[57] ABSTRACT

A transdermal communication apparatus and method is disclosed which utilizes a Hall Effect sensor to be implanted within a body and which acts to receive communication transmissions from an externally placed source. The sensor provides improvements relative to the ease of implantations, reliability, speed of processing, and communication integrity.

21 Claims, 1 Drawing Sheet

METHOD AND APPARATUS FOR TRANSDERMAL COMMUNICATION

BACKGROUND OF THE INVENTION

1. Field of the Invention

This invention relates to a method and apparatus for transdermal communication, and more particularly, to a method and apparatus which allows an implanted device within a body to communicate through a plurality of layers to an externally placed control unit.

2. Discussion

Transdermal communication systems have been used in a wide variety of applications in which communication between an externally placed device and a device implanted within an organism's body (i.e., such as that of a human) was necessary. These systems normally utilized an implanted electrical coil which was electronically coupled to the implanted device. Another coil was then coupled to the externally placed device and was electronically excited so as to produce a signal which was modulated and was within the radio frequency range. This modulated signal passed through a plurality of skin layers associated with the body and was received by the implanted coil. This received signal usually contained a plurality of coded information and produced a magnetic field around the implanted coil which caused the coil to produce a current Which was used to power the implanted device and activate various auxiliary devices associated therewith or which was demodulated causing the coded information to be received by the implanted device. Other past embodiments have used a frequency shift keying (FSK) technique to transfer coded information from the external coil to the implanted device while utilizing a concomitant type of standard radio frequency shift keying modulation and demodulation circuitry.

Many of these past systems have suffered from significant drawbacks in that the implanted coils were usually physically large when compared to the surrounding elements contained within the body and thusly were frequently difficult to implant since in many cases, the required implantation area was quite small. In some cases damage was done, to the body, during implantation.

These past systems also suffered from transmission errors due to their analog designs and were very susceptible to component failure due to the complex circuitry associated with the necessary modulation and demodulation functions and to significant delays especially when used in conjunction with digitally based implanted devices.

SUMMARY OF THE INVENTION

According to the teachings of the present invention a Hall Effect sensor may replace the implanted coil wherein said sensor may be electronically coupled to the implanted device such that electrical power and/or electronic data signals may be transferred thereto upon receipt of magnetic flux energy associated with the coil of the externally placed device. The Hall Effect sensor may further contain a concentrator which increases the sensitivity and response of the sensor to the impressed magnetic flux field by bending the flux lines such that they are directed to the sensor.

Since the Hall Effect sensor is much smaller then the previously used coils, the sensor is both easier to implant and danger of damage to the surrounding area is also correspondingly minimized.

Additionally, the use of the Hall Effect sensor requires no modulation or demodulation circuitry thusly making the communication system simpler and more reliable. The sensor's direct use of digital communications also results in faster system response and allows for greater error correction associated with the transmitted data.

These and other aspects, features, advantages, and objects of this invention will be more readily understood upon reviewing carefully the following detailed description taken in conjunction with the accompanying drawings and claims.

BRIEF DESCRIPTION OF THE DRAWINGS

For a more complete understanding of the present invention relative to the advantages thereof, reference is now made to the following description taken in conjunction with the accompanying drawings in which.

DETAILED DESCRIPTION OF THE INVENTION

Figure 1:
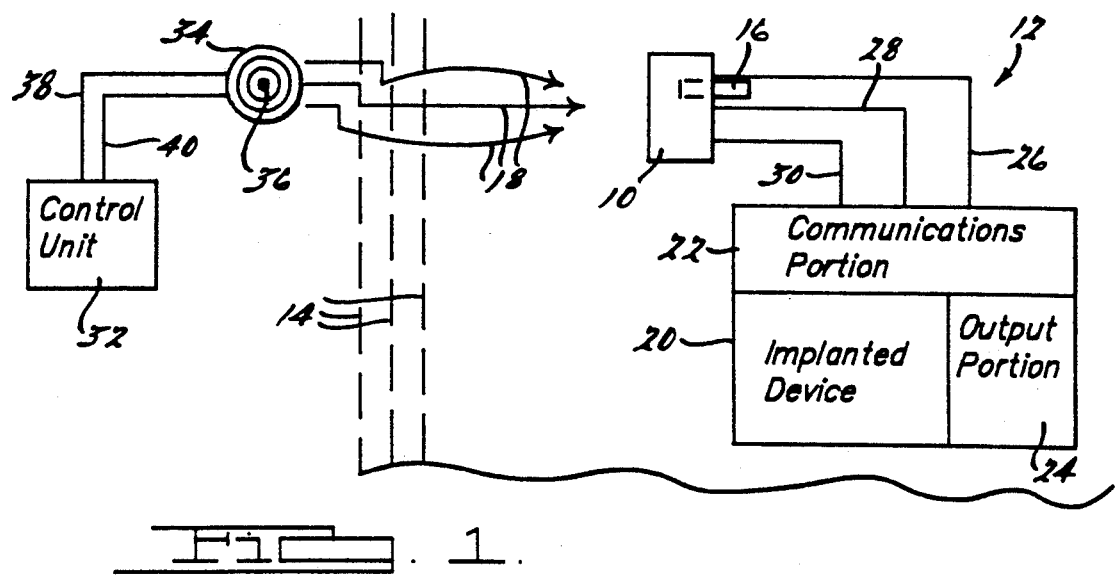
FIG. 1 is a block diagram illustrating the preferred embodiment of this invention.

Referring now to FIG. 1, the Hall Effect sensor 10 is shown as implanted within a body of an organism (i.e. such as a human body) 12 such that sensor 10 is separated from the outside environment of body 12 by a plurality of skin layers 14. Sensor 10 may be implanted within body 12 by a variety of standard surgical techniques. Sensor 10 is a standard Hall Effect sensor and, in the preferred embodiment of this invention, provides linear voltage output characteristics.

Hall Effect sensors are currently available in packages measuring just a few millimeters square. Still smaller surface mount packages are additionally available. The small dimensions associated with these Hall Effect sensors make them easy to implant and minimize the risk of bodily damage during implantation. Additionally, the average switching times associated with such a Hall Effect sensor 10 has been found to be approximately 400 nanoseconds which corresponds to a digital data transfer rate of approximately 1 megabit per second representing a very fast flow of data. Activation flux densities associated with various digitally implanted devices range generally from approximately 95 Gauss to approximately 750 Gauss while deactivation flux densities range from −95 Gauss to approximately 100 Gauss. These Hall Effect sensors have been proven to work well in these ranges.

Sensor 10 is further shown as having a usual concentrator portion 16 which is normally aligned with an axis of incoming magnetic flux lines 18 in the usual manner. Concentrator portion 16 acts to bend or focus flux lines 18 upon sensor 10 thusly increasing the sensitivity and responsiveness thereof.

Implanted device 20 is shown as being in close proximity to sensor 10 and is shown as having the usual communication portion 22 and output portion 24. Portion 24 is used to electronically couple device 20 with an auxiliary device such as an electrode. Portion 22 is used to electronically couple device 20 to a communication source such as an implanted coil (not shown) or to a Hall Effect sensor 10 as used in the preferred embodiment of this invention. As shown, sensor 10 is coupled to portion 22 by signal on lines 26-30 in a substantially similar manner in which an implanted coil was so coupled.

External control unit 32 is shown as electronically coupled to externally positioned coil 34 having a plurality of turns and a magnet 36. Magnet 36 has a two fold purpose in this embodiment. First magnet 36 enhances the concentration of flux lines 18 around sensor 10. This enhanced concentration enables a smaller type of externally positioned coil 34 to be used as well as allowing control unit 32 to utilize less electrical power. Secondly, magnet 36 may be used to hold coil 34 in place during data transmission. This a common practice where a second magnet or piece of ferrous metal (not shown) is required to be implanted within body 12. Coil 34 can then be magnetically attracted thereto and held in place. Coil 34 is electronically coupled to unit 32 by signals on lines 38 and 40.

Magnet 36 may be of a variety of types in the preferred embodiment of this invention such as a Samarium Cobalt type, Alinco 8 type, or Plastalloy type. Each of these aforementioned magnets have unique characteristics associated with magnetic flux degradation across an air gap separating the magnet 34 from the Hall Effect sensor 10. The table below details the degradation characteristics of each of the aforementioned magnets:

| Airgap | Magnet Type | | |
|---|---|---|---|
| | Samarium Cobalt | Alinco 8 | Plastalloy |
| 2.54 mm | 150 Gauss | 235 Gauss | 290 Gauss |
| 3.81 mm | 65 Gauss | 135 Gauss | 180 Gauss |
| 5.08 mm | 20 Gauss | 85 Gauss | 120 Gauss |
| 6.35 mm | 5 Gauss | 65 Gauss | 90 Gauss |

In operation, control unit 32 excites coil 34 by an electrical signal on lines 38 and 40. This excitation in co-operation with magnet 36 causes a plurality of magnetic flux lines 18 to be generated. No radio frequency or frequency shift keying modulation is needed. Flux lines 18 penetrate skin layers 14 and are received by concentrator 16 which causes flux lines 18 to be received by sensor 10.

Upon receipt of flux lines 18, sensor 10 produces a voltage signal on lines 26-30 which is received by portion 22. Signal on lines 26-30 may itself represent digitally encoded information, such as programming data, or may be directed to output portion 24, by portion 22, so as to power auxiliary devices coupled thereto.

Figure 2:
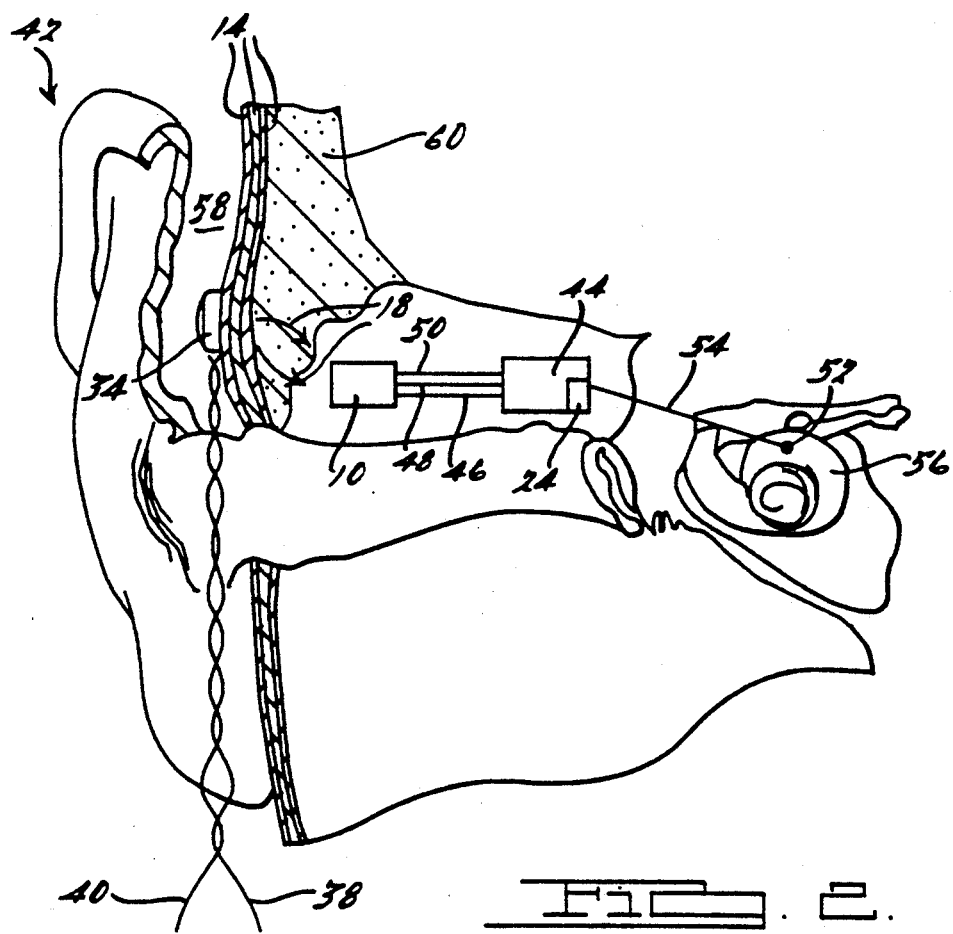
FIG. 2 is an illustration of the use of this, the preferred embodiment of this invention within a human ear.

Referring now to FIG. 2, Hall Effect sensor 10 is shown as implanted within a human ear 42 such that it is electronically coupled to a typical implanted Cochlea stimulating hearing aid 44 by signals on lines 46-50. In this embodiment, device 44 is electronically coupled to an electrode auxiliary output device 52 by signal on line 54 which terminates within portion 24. Device 52 is attached to the Cochlea 56, of ear 42, in the usual manner and stimulates the same.

In this embodiment, coil 34 is physically placed into an upper portion 58, of ear 42 and signal lines 38 and 40 are made to extend downward alongside ear 42 and eventually into control unit 32 which may be placed in a shirt pocket. Flux lines 18 are generated, in the manner alluded to earlier, and represent digital data. Lines 18 penetrate ear 42 and skull portion 60 having a plurality of skin layers 14. Flux lines 18 are received by sensor 10 in the manner previously specified, and digital data in the form of electrical voltage is coupled through signals on lines 46-50 to device 44 in order to direct the control of device 52.

It should be appreciated that the transmission and reception of data in this embodiment may be accompanied by standard types of cyclical redundancy parity bits or other types of error correcting data in order to provide highly secure transmissions.

Although a single embodiment of this invention has been illustrated in the accompanying drawings and described in the forgoing details of the description, it will be understood that the invention is not limited to the embodiment disclosed, but is capable of numerous rearrangements, modifications, and substitutions without departing from the scope of the subjoined claims associated with the aforementioned invention.

I claim:

1. A method for transdermal communication between an external control unit having a source of magnetic energy and an implanted device implanted within and surrounding by a plurality of skin layers, said method comprising implanting a Hail Effect sensor within and surrounded by the layers of skin, having an input and output, in close proximity to the implanted device wherein said implanted device has an input; coupling said output of said Hail Effect sensor to said input of said implanted device; and magnetically coupling a source of magnetic energy from the external control unit outside of the layers of skin to said input of said Hall Effect sensor thereby allowing the external control unit to transdermally communicate with said implanted device.

2. The method of claim 1 further comprising providing a concentrator; and coupling said concentrator to said input of said Hall Effect sensor.

3. The method according to claim 1 wherein said coupling steps include transmitting a digital signal to said implanted device.

4. The method as defined in claim 3 wherein said transmitting step includes transmitting bits at a rate of about 1 megabit per second.

5. The method according to claim 1 wherein said enternal control unit generates a digital signal controlling said implanted device.

6. The method according to claim 1 wherein said external control unit generates a signal directed to an output of said implanted device.

7. A method for transdermal communication between an external control unit having a source of magnetic energy and a bearing aid device implanted within a portion of a body of an organism wherein the body has a plurality of skin layers and wherein the implanted bearing aid device is substantially surrounded by said plurality of skin layers, said method comprising implanting a Hall Effect sensor, having an input and output, within the body and in close proximity to the implanted bearing aid device; coupling a concentrator to said input of said Hall Effect sensor; transdermally coupling the source of magnetic energy of the external control unit to said concentrator; and coupling said output of said Hall Effect sensor to said implanted bearing aid device thereby allowing the external control unit to transdermally communicate with said implanted bearing aid device.

8. A method for transdermal communication between an external control unit having a source of magnetic field and a bearing aid device, wherein the bearing aid device is implanted within an ear and is substantially surrounded by a plurality of layers of skin, said method comprising implanting a Hall Effect sensor, having an input and output, under said plurality of layers of skin within the ear; coupling said output of said Hall Effect sensor to the bearing aid device; and coupling the magnetic field of the external control unit to said input of said Hall Effect sensor thereby allowing the external control unit to transdermally communicate with said implanted bearing aid device.

9. The method of claim 8 further comprising providing a concentrator; and coupling said concentrator to said input of said Hall Effect sensor.

10. A transdermal receiver allowing communication between a bearing aid device implanted within and surrounded by a plurality of skin layers and an external device outside of the plurality skin layers comprising a Hall Effect sensor implanted within and surrounding by the plurality of skin layers; means for coupling said sensor to the implanted bearing aid device; and means for magnetically coupling said sensor to the external device for transdermal communication between said implanted bearing aid and said external device.

11. The device of claim 10 wherein said magnetically coupling means comprises a concentrator.

12. The device of claim 10 wherein said sensor comprises a linear output Hall Effect sensor.

13. A transdermal communication device for communicating between a device implanted within a body under a plurality of skin layers and an external control means having a source of magnetic energy, comprising Hall Effect sensor means, having an input and output, for placement within the body and under a plurality of skin layers and for transdermally coupling the source of magnetic energy from the external control means to the implanted device; first coupling means for coupling said output of said Hall Effect sensor means to said implanted device; and second coupling means for magnetically coupling said input of said Hall Effect sensor means transdermally to said source of magnetic energy from said external control means.

14. The device of claim 13 wherein said second coupling means comprises a concentrator.

15. The device according to claim 13 wherein said external control means comprises a control unit for transmitting a digital signal.

16. The device as defined in claim 15 wherein said control unit has means for transmitting a magnetic flux representing said digital signal.

17. A transdermal receiver for communication between a bearing aid implanted within an ear under a plurality of layers of skin above the ear canal, and an external control unit, comprising a source of magnetic energy from the external control unit, a Hall Effect sensor means, having an input, implanted within the dermal layer surrounding the ear canal for coupling said source of magnetic energy to the implanted bearing aid; first coupling means for communicating a signal from said sensor to said implanted bearing aid; and second coupling means for magnetically coupling said source of magnetic energy to said input of said sensor.

18. The device of claim 17 wherein said second coupling means comprises a concentrator.

19. The device of claim 17 wherein said sensor comprises a linear output Hall Effect sensor.

20. A transdermal communication device allowing communication between a medical device implanted under a plurality of skin layers and an external device having transmitting means outside of said plurality of skin layers, said transdermal communication device comprising a Hall Effect sensor implanted under the plurality of skin layers, means for coupling the sensor to the implanted medical device, and the transmitting means of the external device having a control unit generating magnetic flux penetrating the plurality of skin layers for transdermally communicating between said external device and said implanted medical device.

21. A transdermal communication device for communication between a medical device, implanted under a plurality of layers of skin, and an external control unit, comprising an external control unit outside of the plurality of skin layers for generating magnetic flux penetrating the skin layers, a Hall Effect sensor means implatned under a plurality of skin layers for coupling said magnetic flux to the implanted medical device, coupling means for communicating a signal from said sensor to said implanted device, and a concentrator for magnetically coupling said magnetic flux from said external control unit to said Hall Effect sensor for transdermally communicating between said external control unit and said implanted medical device.

* * * * *